United States Patent
Sandhu

(10) Patent No.: US 10,512,592 B1
(45) Date of Patent: Dec. 24, 2019

(54) MEDICATION DISPENSER

(71) Applicant: Amanpreet Sandhu, Chambersburg, PA (US)

(72) Inventor: Amanpreet Sandhu, Chambersburg, PA (US)

(\*) Notice: Subject to any disclaimer, the term of this patent is extended or adjusted under 35 U.S.C. 154(b) by 0 days.

(21) Appl. No.: 15/783,931

(22) Filed: Oct. 13, 2017

(51) Int. Cl.
| | |
|---|---|
| *A61J 7/00* | (2006.01) |
| *A61J 7/04* | (2006.01) |
| *G07F 17/00* | (2006.01) |
| *A61B 5/1172* | (2016.01) |
| *A61K 31/485* | (2006.01) |

(52) U.S. Cl.
CPC .......... *A61J 7/0076* (2013.01); *A61J 7/0481* (2013.01); *A61B 5/1172* (2013.01); *A61J 7/0445* (2015.05); *A61J 2200/30* (2013.01); *A61K 31/485* (2013.01); *G07F 17/0092* (2013.01)

(58) Field of Classification Search
CPC .............................. A61J 7/0076; A61J 7/0481
USPC ......................................................... 700/237
See application file for complete search history.

(56) References Cited

U.S. PATENT DOCUMENTS

| | | | | |
|---|---|---|---|---|
| 7,392,918 B2 * | 7/2008 | Holloway | ................. | A61J 1/03 |
| | | | | 221/151 |
| 9,439,835 B2 * | 9/2016 | DiMartino | ............ | A61J 7/0076 |
| 9,913,778 B2 * | 3/2018 | Dvorak | ................. | A61J 7/0084 |
| 9,928,348 B2 * | 3/2018 | Kreiner | ............... | G06F 19/3462 |
| 10,073,954 B2 * | 9/2018 | Chen | ......................... | A61J 1/03 |
| 10,124,940 B2 * | 11/2018 | Blackburn | ............. | G16H 20/13 |
| 10,223,505 B2 * | 3/2019 | Meyers | ............... | G06F 19/3462 |
| 10,328,469 B1 * | 6/2019 | Shah | .................... | B09B 3/0075 |
| 2009/0223994 A1 * | 9/2009 | Getz | ..................... | A61J 7/0076 |
| | | | | 221/154 |
| 2010/0318218 A1 * | 12/2010 | Muncy, Jr. | .......... | G06F 19/3462 |
| | | | | 700/220 |
| 2014/0074283 A1 * | 3/2014 | Blackburn | ............ | A61J 7/0076 |
| | | | | 700/237 |
| 2016/0158107 A1 * | 6/2016 | Dvorak | ................. | A61J 7/0084 |
| | | | | 241/25 |

\* cited by examiner

*Primary Examiner* — Albert K Wong

(57) ABSTRACT

This invention relates to a tamper resistant medication dispenser. The medication dispenser is programmed to dispense a specified dose of medication at a specified interval. The medication dispenser prevents direct access to the medication by the patient. The medication is dispensed to the patient dissolved in a large volume of liquid to prevent intravenous and intranasal abuse. The medication dispenser can be equipped with a self destruct mechanism when tampered with and have the ability to record video for subsequent monitoring, the actual medication ingestion of the medication infused liquid by the patient. It is especially useful for controlled substances which have high potential for abuse such as opioids, benzodiazepines and barbiturates and anesthetic agents and when patient compliance with medications is necessary such as medications for the treatment of contagious diseases.

8 Claims, 14 Drawing Sheets

Fig. 1

MEDICATION DISPENSER

Figure 1:
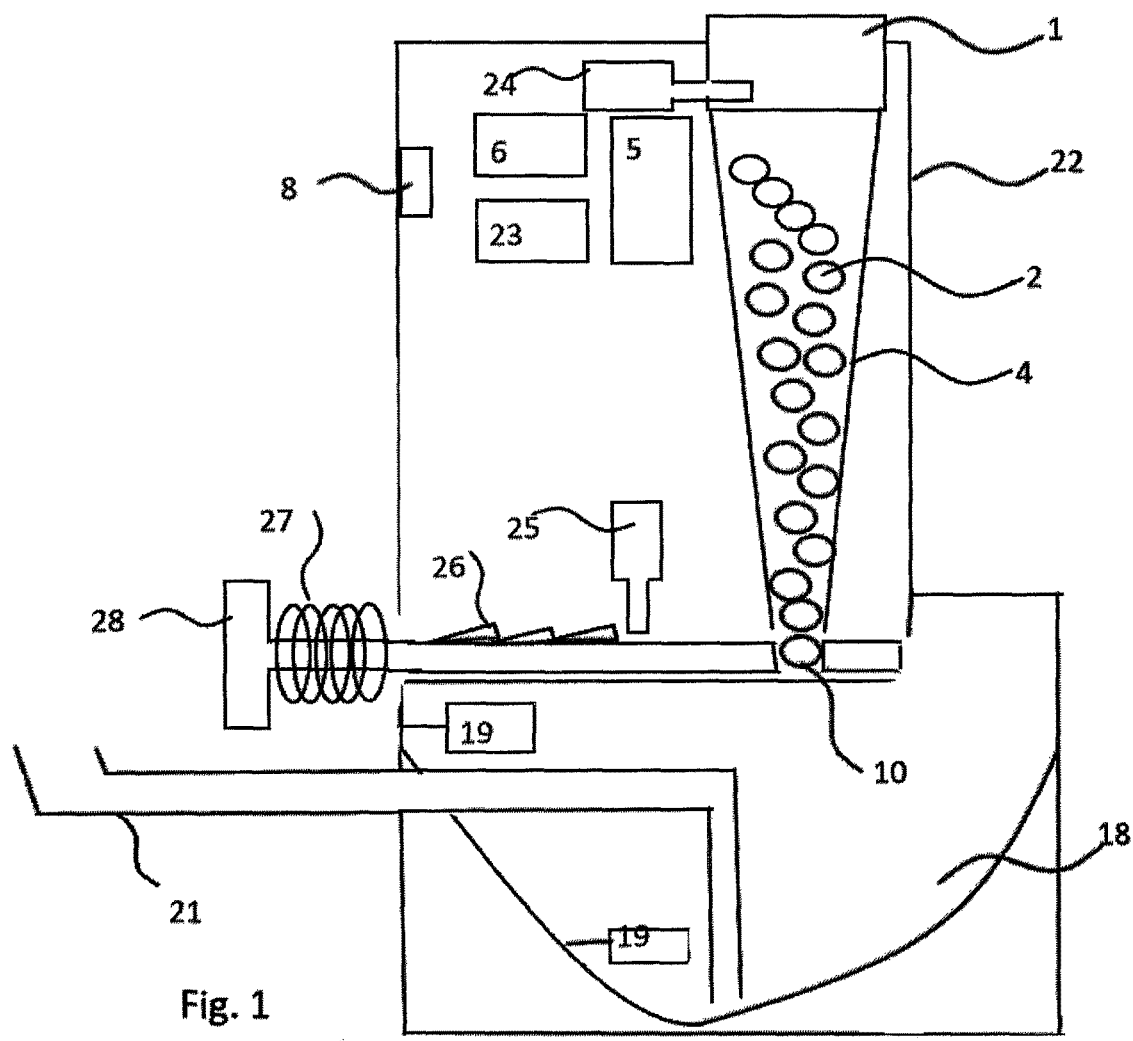

This invention relates to a tamper resistant medication dispenser. The medication dispenser is programmed to dispense a specified dose of medication at a specified interval. The medication dispenser prevents direct access to the medication by the patient. The medication is dispensed to the patient dissolved in a large volume of liquid to prevent intravenous and intranasal abuse. The medication dispenser can be equipped with a self destruct mechanism when tampered with and have the ability to record video for subsequent monitoring, the actual medication ingestion of the medication infused liquid by the patient. It is especially useful for controlled substances which have high potential for abuse such as opioids, benzodiazepines and barbiturates and anesthetic agents and when patient compliance with medications is necessary such as medications for the treatment of contagious diseases.

CROSS-REFERENCE TO RELATED APPLICATIONS

Patent Applications Nos. 62/496,305 and 62/497,130
This application claims the benefit of PPA #62/496,305, filed Oct. 13, 2016 and PPA #62/497,130 filed Nov. 10, 2016 by the present inventors, which is incorporated by reference.

FEDERALLY SPONSORED RESEARCH

Not Applicable

BACKGROUND

This application relates to medication dispenser, specifically an improved abuse resistant medication dispenser.

prescription medication overdose, misuse and abuse are one of the leading causes of death in USA with almost 168,000 Americans having died from medication overdose in the last 10 years. More Americans and dying from drug overdose than from car accidents. Opioid use disorders resulted in 51,000 worldwide deaths in 2013 up from 18,000 deaths in 1990. Prescription opioid overdose was responsible for more deaths in the United States from 1999-2008 than heroin and cocaine overdose combined.

Patient's a generally prescribed opioids and benzodiazepines in 1 month supply. Patients suffering from opioid abuse and benzodiazepine addiction frequently abuse and misuse of medications by various routes including ingesting medications in doses significantly more than prescribed, crushing pills and chewing them, snorting them, injecting them as well as rectal administration in order to achieve a rapid release of the medication to achieve a drug high. This frequently leads to overdose and respiratory depression and death. Once the medications are dispensed from the pharmacy there are no checks or balances that would prevent this kind of abuse. Pharmaceutical companies have tried to mitigate some of the abuse by making medications abuse resistant that are difficult to snort or inject however many of these abuse deterrent mechanisms can be easily bypassed or the patient can simply ingest several days worth of medications at one time in order to achieve a drug high and risking death from overdose. For example a patient was prescribed oxycodone 5 mg 4 times a day will have 120 pills dispensed for one-month supply. Once dispensed from the pharmacy the patient can take some or all 120 pills at one time or sell some or all of his medications.

PRIOR ART

Method and device for pill dispensing U.S. Pat. No. 7,392,918 B2
Drug Delivery Regulator US 2014/0074283 A1
Biometric electronic communicating drug dispenser U.S. Pat. No. 9,439,835 B2
Thumb/Fingerprint activated pill dispenser US2009/0223994 A1
Pill dispenser and method US2010/0318218 A1
Prescription medication security and dispensing systems US20160158107 A1

Disadvantages of Prior Art

All prior art dispenses the medications directly to the patient and have no way to ensure that the patient actually consumes the dispensed medication rather than just storing it one pill at a time for subsequent misuse or abuse once

Advantages

The medication dispenser claimed here
Allows the patient to access only one dose of medication at a pre programmed dosing interval
Medication is dispensed to the patient only infused in liquid of a quantity that is too large to inject or abuse intranasally and as has added gelling agents to prevent further abuse or misuse
Actual ingestion of the medication infused liquid by the patient can be video recoded for subsequent review
Patient never have direct access to the medication
Can be tamper resistant with a self destruct mechanism which inactivates the medication, if the device detects any attempts at tampering with the device
Can be use a smartphone or computer as the electronic control unit and use biometric access controls available on these devices such as password locking, fingerprint, iris scanning, face scanning access controls such as touch ID and face ID and other future technologies to prevent access to medication by anyone other than the patient
Can be programmed to deactivate the remaining unused medication once a specified interval has passed and the medication is no longer medically necessary via cellular networks

SUMMARY

Drawings

Figure 2:
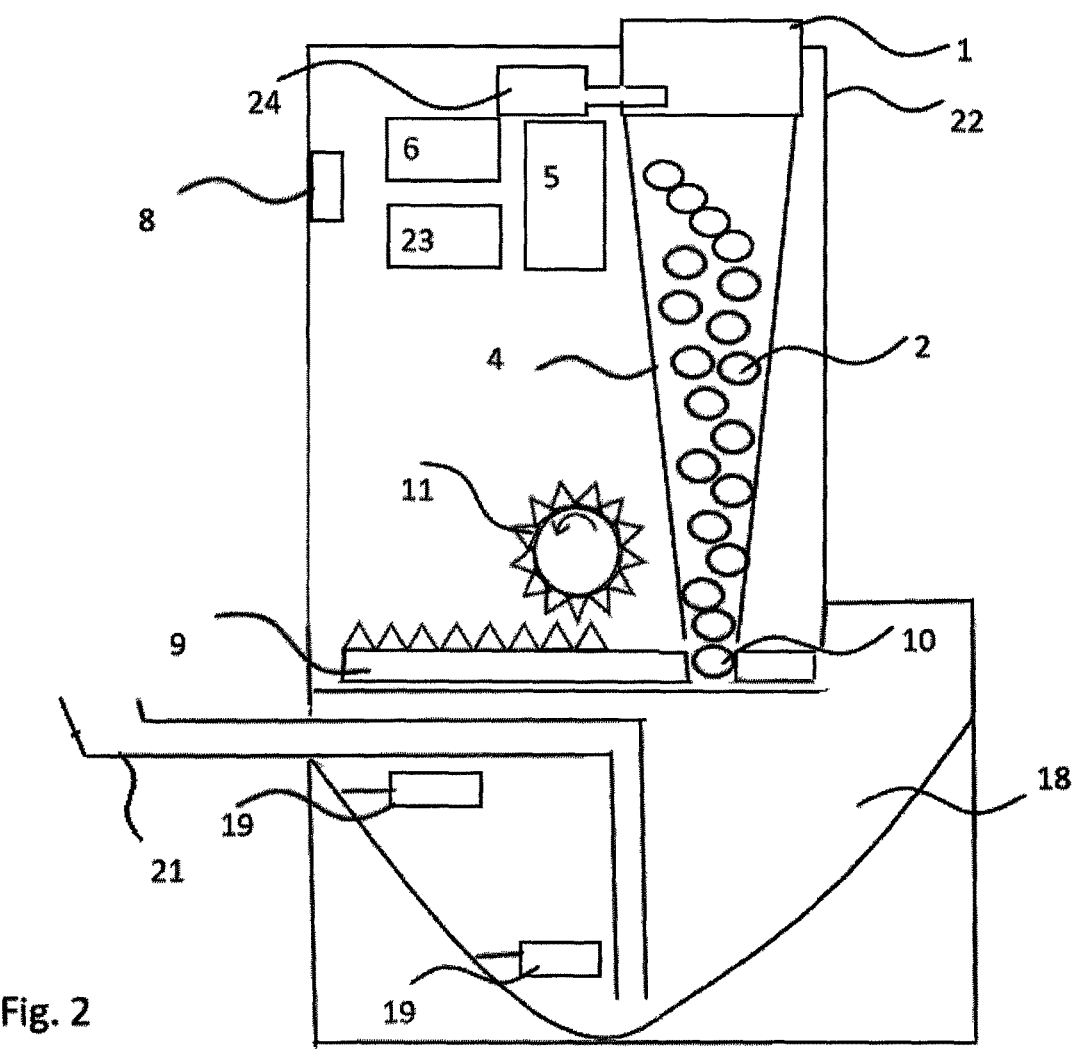
Figure 3:
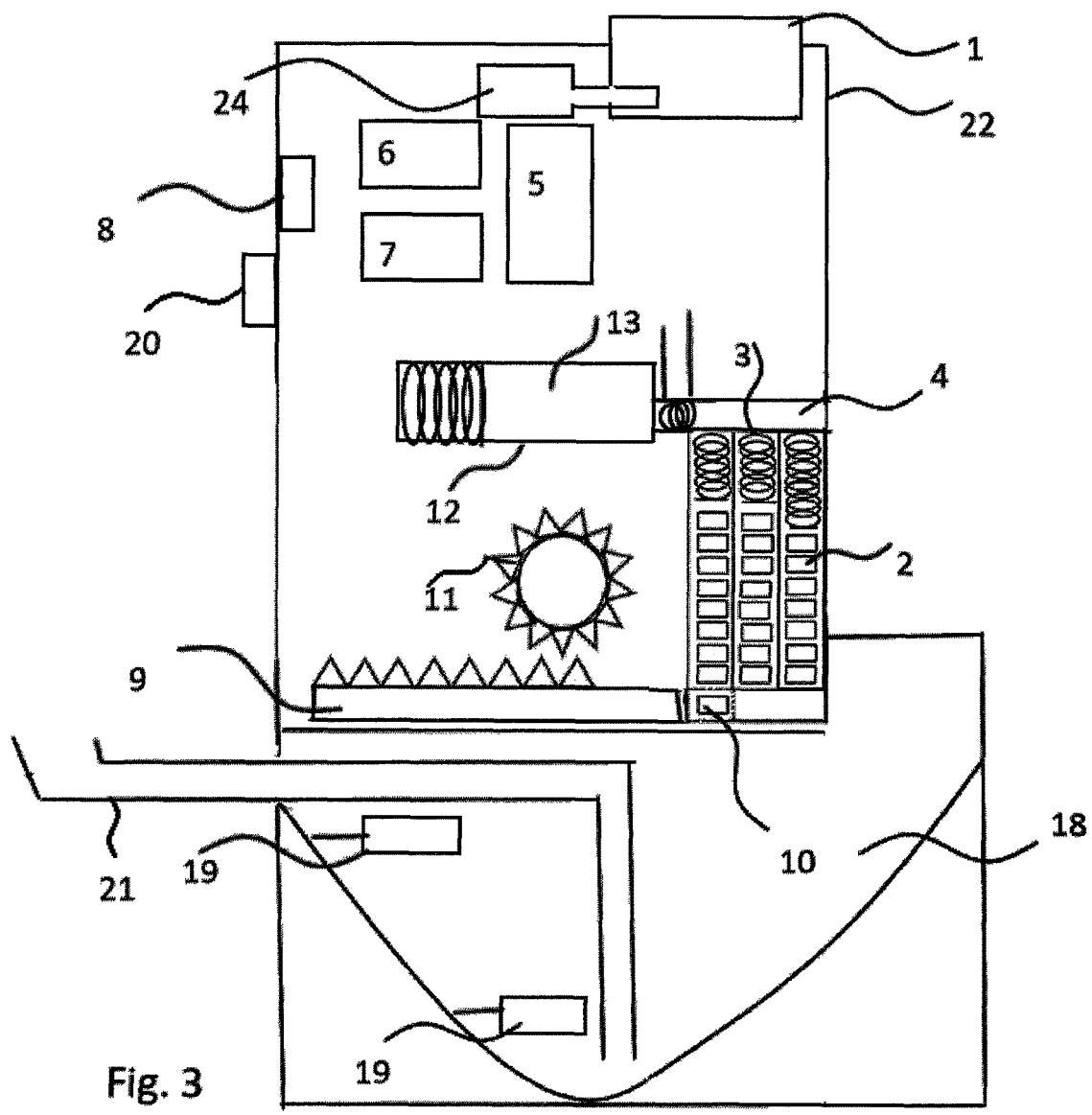
Figure 4:
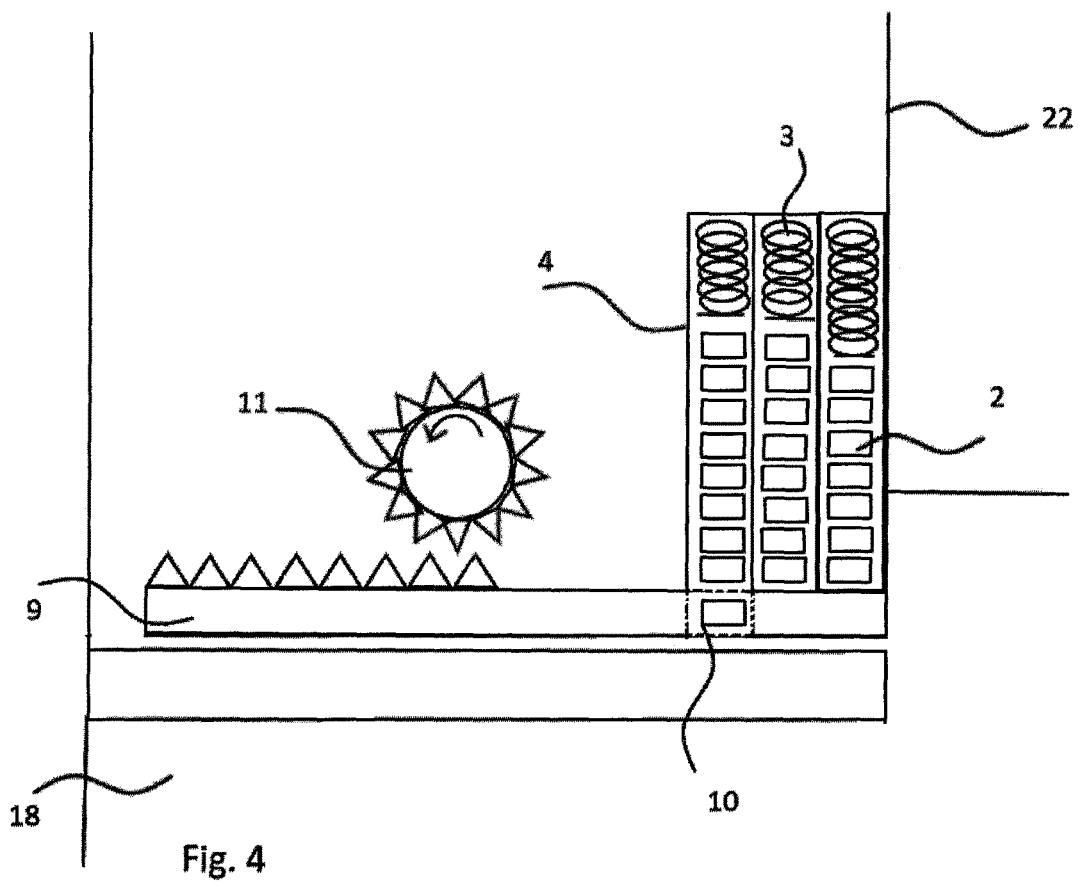
Figure 5:
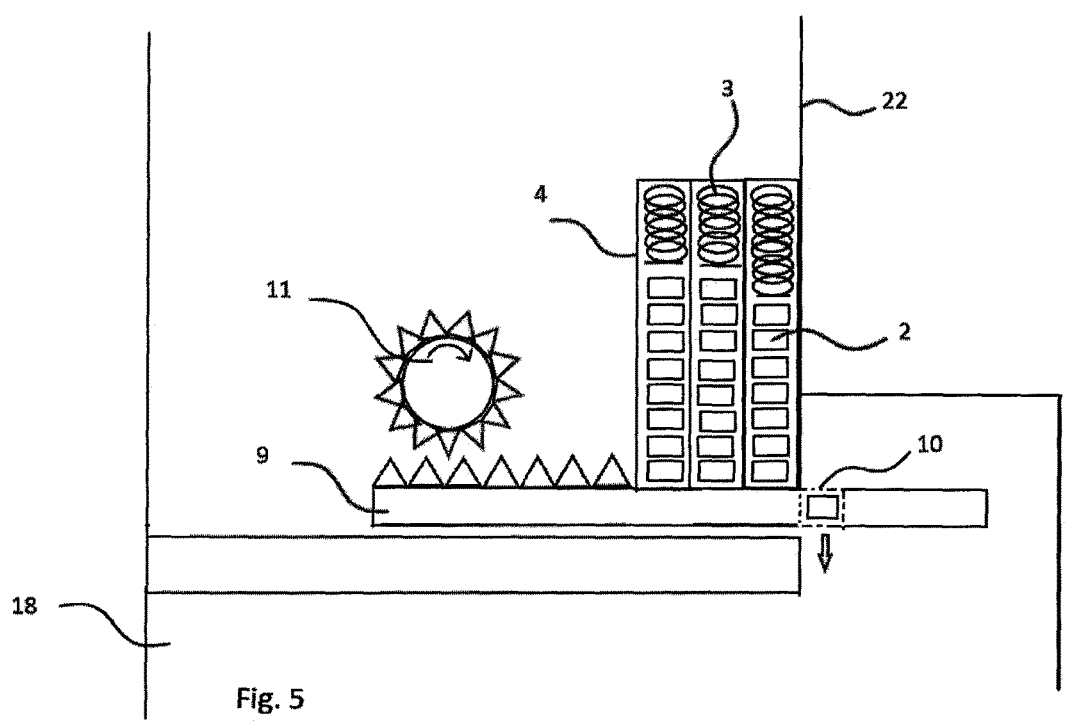

FIG. 1
Cross sectional view of manual push button activated medication dispenser with liquid reservoir 18 for pills 2
FIG. 2
Cross sectional view of electronically activated medication dispenser with liquid reservoir 18 for pills 2
FIG. 3
Cross sectional view of smartphone controlled tamper proof electronically activated medication dispenser with liquid reservoir 18 for pills 2 with video recording and chemical deactivation system 12
FIG. 4 and FIG. 5
Cross sectional views showing the dispensing of pills into the liquid reservoir 18 for electronically activated dispensing system for pills for medication dispensers in FIG. 2 and FIG. 3

FIG. 6

Cross sectional view of medication deactivation system 12

Figure 7:
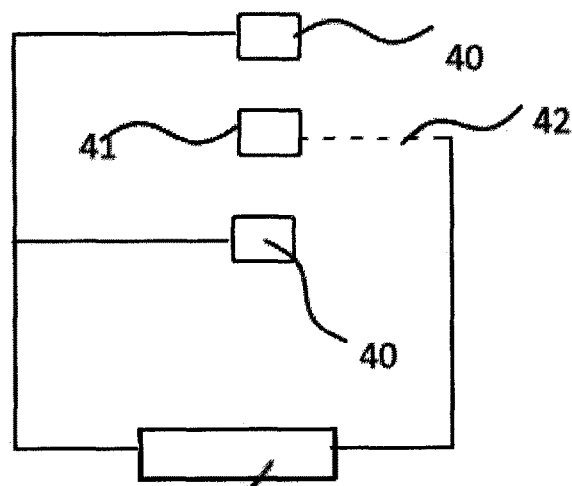
Figure 7:
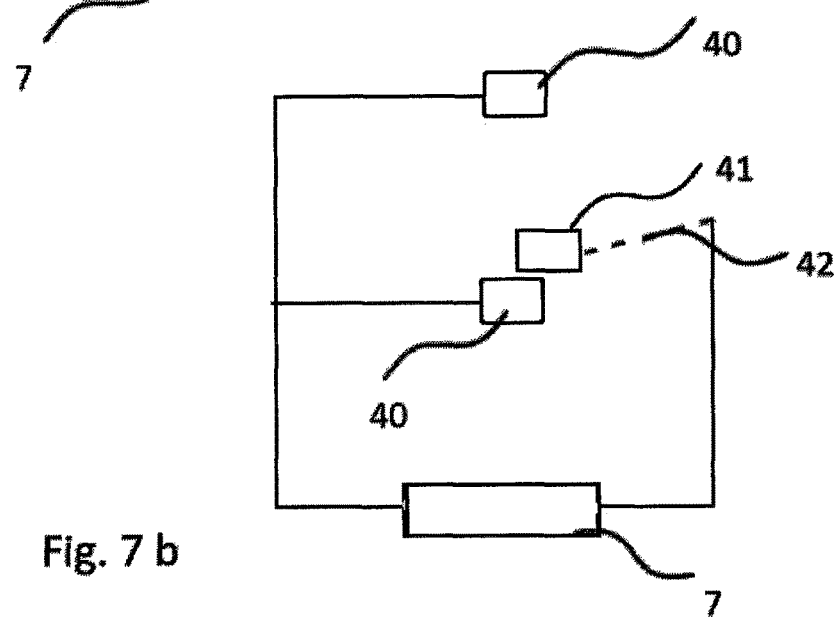

FIGS. 7a and 7b

Schematic of passive shock and magnetic sensors

Figure 8:
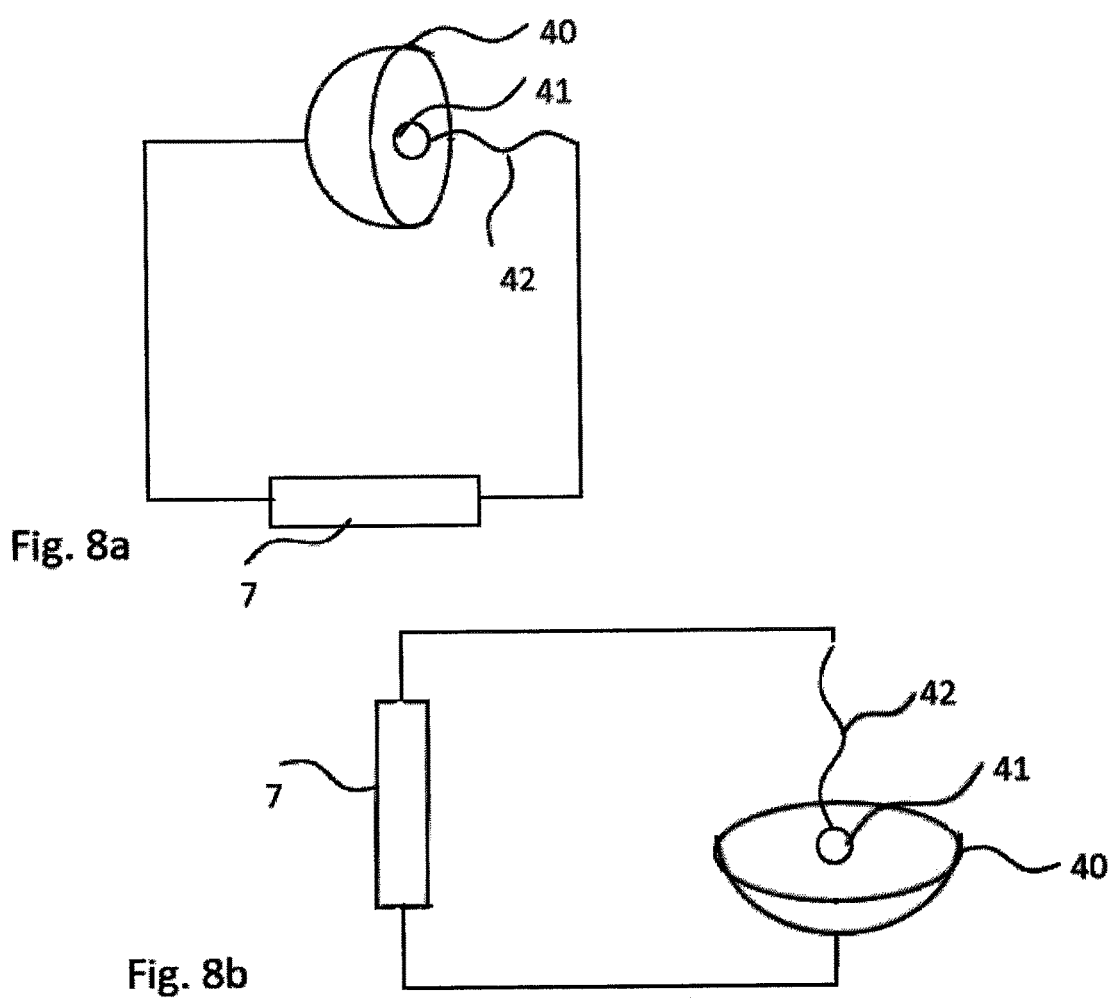

FIGS. 8a and 8b

Cross sectional view of passive shock and magnetic sensors in vertical plane FIG. 8a and horizontal plane FIG. 8b

FIG. 9

Schematic of wire break/trip wire circuit perforation sensor

FIG. 10

Angled view of pill medication dispenser with pill tubes 32 arranged in a circle and stepper motor controlled circular disc with pill slot 10 and dispensing chute 11

FIG. 11

Cross sectional view of tamper proof manual push button activated medication dispenser for pills with video recording

FIG. 12

Cross sectional view of smartphone controlled tamper proof electronically activated medication dispenser with liquid reservoir 18 for liquid medication with video recording and chemical deactivation system 12

FIG. 13

Figure 12:
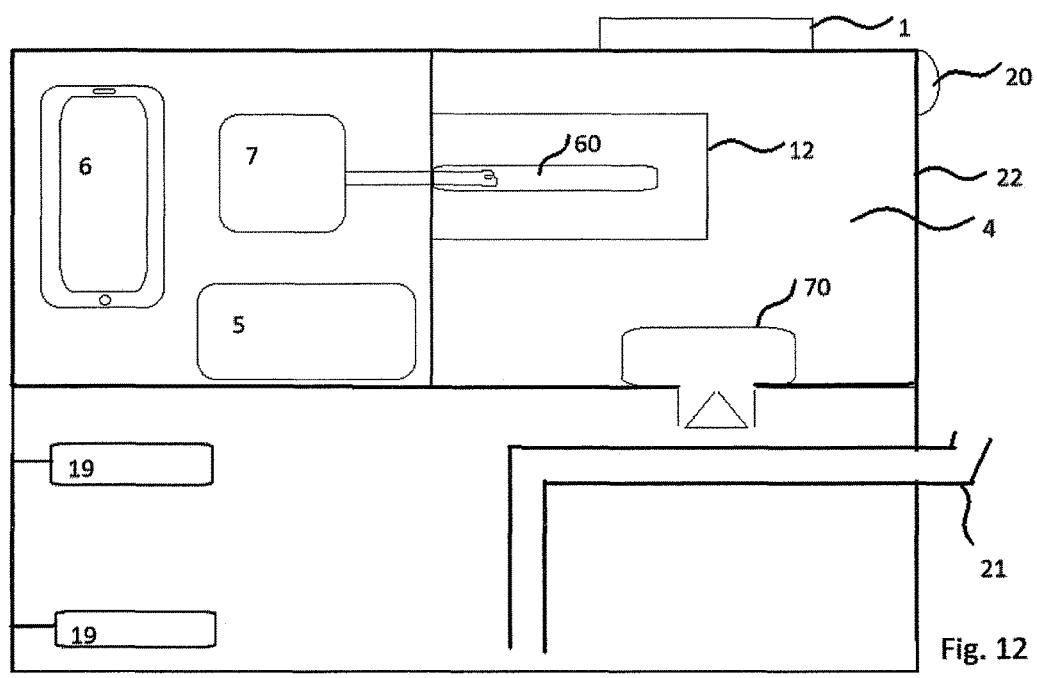

Cross sectional schematic of chemical medication deactivation system for medication dispenser in FIG. 12

FIG. 14

Cross sectional view of smartphone controlled tamper proof electronically activated medication dispenser for liquid medication with flowmeter and video recording and chemical deactivation system

DETAILED DESCRIPTION

In accordance with one embodiment as shown in FIG. 1, the medication dispenser is a portable unit and consists of a lockable container incorporating a locking cap 1 and lock 24 a medication chamber 4 to hold medications for dispensing the medications 2 are spherical shaped rapidly dissolving pills a programmable electronic control unit (ECU) 6 with a timer and dispense button 23, to allow for dispensing of a preprogrammed dose of medications at preprogrammed intervals a manually operated push button dispensing arm 28 has ratchet teeth 26 and a through and through pill slot 10, sized to just hold one pill at a time. The push button dispensing arm is locked at baseline using an electronic lock such as a solenoid lock 25 and unlocked by a signal from the programmable electronic control unit 6 a liquid reservoir 18 into which the medication 2 is dispensed the liquid reservoir 18 has a port 21 to pour liquid in and subsequently drink the medication infused liquid and is designed to allow the medication infused liquid to be orally suctioned but not poured out upper and lower float switches 19 to monitor filling and emptying of the liquid reservoir by the programmable control unit 6

Method of Operation

The medication dispenser is a lockable and reusable unit that is loaded with medications 2 and is programmed by the dispensing pharmacist via a communication port such as usb port to allow for dispensing of one dose of medication 2 at a preprogrammed interval. Only the dispensing pharmacist has access to the key used to lock 24 and unlock the locking cap 1 that allows access to the medication chamber 4 and the communication port for programming the device. Multiple interchangeable lids with different key combinations are used each month to deter duplication of the lock key by the patient. The ECU 6 can also record every time the locking cap 1 is opened by using a normally closed switch when the locking cap 1 is closed and turning the switch on when the locking cap 1 is opened.

At baseline the push button dispensing arm 28 is held in the locked position by the locking bar of the solenoid 25 acting as a ratchet mechanism. The solenoid 25 is connected to the upper float switch 19 in series.

A count down timer 23 allows the patient to know when the next medication dose is due and the patient fills the liquid reservoir 18, via port 21, causing the upper float switch 19 to close and turn on. The patient presses the dispense button on the ECU 6 causing the solenoid 25 to pull back the locking bar. This unlocks the push button dispensing arm 28 and when the patent pushes it all the way forward one pill located in the pill slot 10 drops into the liquid reservoir 18. The patient lets go of the push button dispensing arm 28 and the return spring 27 returns it back to the baseline position and another pill falls into the pill slot. The final forward movement of the push button dispensing arm 28 activates a push button which signals to the ECU 6 to release the solenoid 25 locking bar and the ratchet mechanism 26 prevents the bar from being pushed forward again. The patient drinks the medication infused liquid by sucking the liquid from the port 21. Once the liquid in the liquid reservoir 18 falls below the lower float switch 19, it signals to the ECU 6 to start the countdown timer until the next medication dose is due.

The push button dispensing arm 28 cannot be unlocked until the liquid reservoir 18 is full and the count down timer for the next dose does not start until the liquid reservoir 18 is empty, based upon signal input from the upper and lower float switches.

The medication dispenser is examined for any attempts at tampering before the next time it is refilled and any evidence of tampering with the medication dispenser would result in discontinuation of any further medication prescribing to the patient.

The medication dispenser has rubber seals including 0 ring seals to prevent water entry into the medication chamber 4 and liquid contact indicators are located inside to detect tampering.

The port 21 design prevents the medication infused liquid from being poured out.

The medication dispenser can also be a single use disposable unit with the locking cap 1 being permanently sealed after loading and closing it shut.

To prevent shock and magnetic tampering a dual solenoid electronic lock can be used. The primary solenoid is held in locked position by a secondary solenoid placed at 90 degrees to the primary solenoid arranged in series, when current is applied to the circuit the arm of the secondary solenoid is withdrawn which allows the primary solenoid to pull the locking plunger back.

PARTS LIST FIG. 1

1 locking cap
2 medication pills
4 medication chamber
5 power supply
6 electronic control unit 8 charging port
10 pill slot
18 liquid reservoir
19 upper and lower float switches
21 port
22 outer wall
23 Dispense timer and switch
24 lock
25 electronic lock
26 ratchet teeth
27 push button dispensing arm return spring
28 push button dispensing arm In another embodiment as shown in FIG. 2 instead of a manually operated push button dispensing arm, a stepper motor controlled by the ECU 6 controls a pinion gear 11 to move the dispensing ratchet arm 9 forwards and backward. The rest of the design and operation is similar to the embodiment shown in FIG. 1.

PARTS LIST FIG. 2

1 locking cap
2 medication pills
4 medication chamber
5 power supply
6 electronic control unit
8 charging port
9 dispensing arm with rack
10 pill slot
11 stepper motor pinion gear
18 liquid reservoir
19 upper and lower float switches
21 port
22 outer wall
23 Dispense timer and switch
24 lock In accordance with another embodiment as shown in FIG. 3 (overview) and details in FIG. 4 through FIG. 10 the medication dispenser is a portable unit and consists of a lockable container incorporating a water tight locking cap 1 and lock 24 a medication chamber 4 has vertical pill tubes, each sized to hold a single vertical row of medication pills 2, with the pill tubes being arranged in a single line. The medication pills 2 are held in place in the pill tubes by spring loaded plungers 3 for controlled feeding into the pill slot 10 which is a through and through hole in the dispensing arm 9. The electronically operated dispensing arm 9 is located at the bottom of the pill tubes and moves back and forth.

Figure 9:
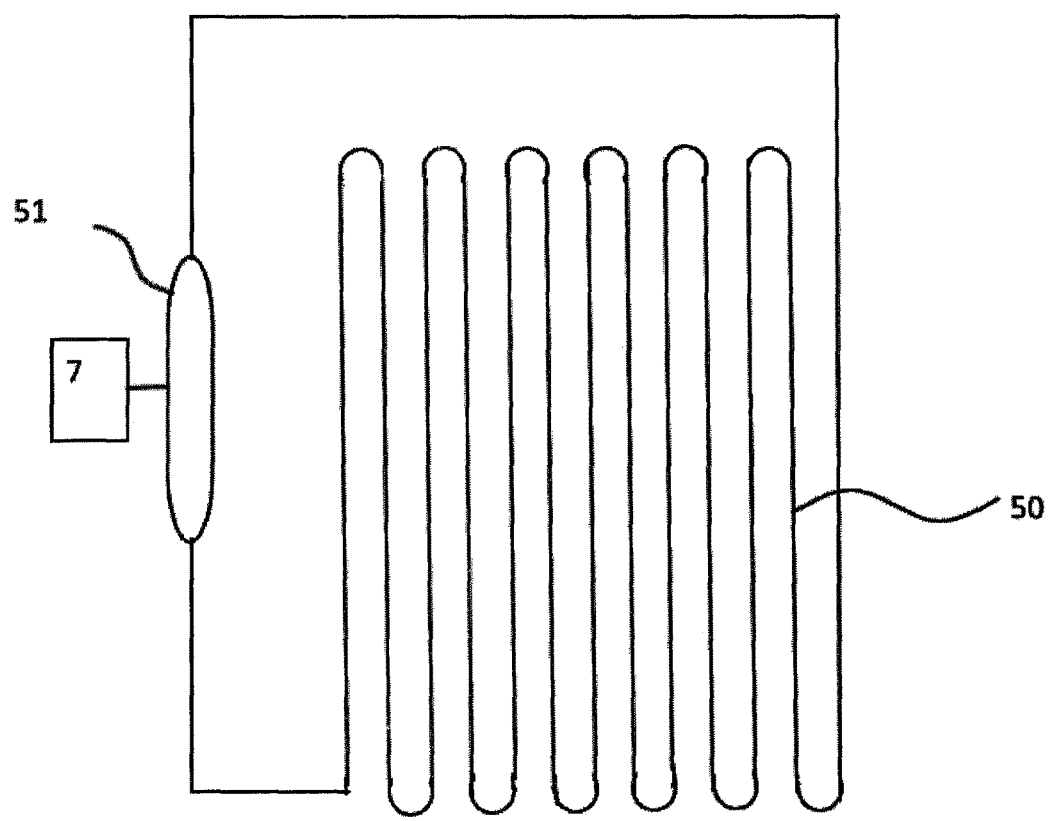

The dispensing arm 9 is connected to an electronically controlled stepper motor 11 rotating a pinion gear connected to the rack on dispensing arm 9 allowing the dispensing arm 9 to move back and forth. The dispensing arm 9 functions as a linear actuator. The pills 2 are pushed against the dispensing arm 9 by spring loaded plungers 3 in each pill tube. The dispensing arm 9 has a slot 10 that is sized so as to be able to hold only one medication pill 2 at a time. When ready to dispense the stepper motor 11 is activated rotating the pinion gear counter clockwise pushing the (rack) dispensing arm 9 forward and out into the liquid reservoir 18 attached to the bottom of the medication dispenser and causing the pill 2 held in the pill slot 10 to drop into the liquid reservoir 18 and then reverse/clockwise movement of the pinion by the stepper motor 11 pulling back the (rack) dispensing arm 9 and loading the pill slot 10 with another pill 2 from the outermost pill tube until it is empty and then from the pill tube next to last, until it is empty and so on and so forth until all the pill tubes are empty, as shown in FIGS. 4 and 5.

the medications 2 are rapidly dissolving pills a smartphone 6 acts as the programmable electronic control unit (ECU) 6 and controls a stepper motor pinion gear 11 to move the dispensing ratchet arm 9 back and forth to allow for dispensing of one medication pill at preprogrammed intervals. The device is controlled using a smartphone app.

the liquid reservoir 18 has a port 21 to pour liquid in and subsequently drink the medication infused liquid and is designed to allow the medication infused liquid to be orally suctioned but not poured out upper and lower float switches 19 to monitor filling and emptying of the liquid reservoir by the programmable control unit 6 back up power supply, secondary ECU and tamper sensors 7 including electronic perforation/break wire/trip sensor FIG. 9, pressure sensors, shock and magnetic sensors FIGS. 7a and 7b and FIGS. 8a and 8b, liquid sensors and temperature sensors are incorporated in the medication dispenser closely spaced loops of break wire/trip circuit perforation sensor FIG. 9 incorporated into all the walls 22 and locking cap 1 of the medication dispenser.

The liquid reservoir 18 at the bottom of the medication dispenser has float switches 19 at the bottom and top of the liquid reservoir 18.

Figure 6:
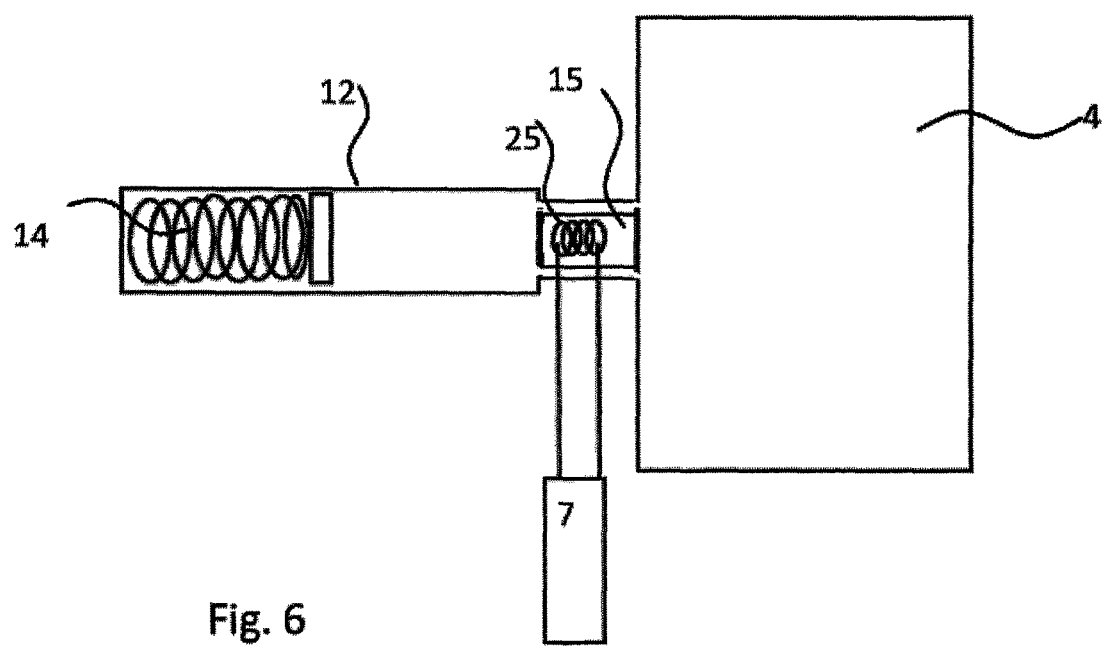

Medication deactivation system 12 consisting of a syringe with a spring loaded plunger FIG. 6, 14. The syringe drains into the medication chamber 4 and is sealed with a wax plug FIG. 6, 15. The syringe 13 is filled with a combination of chemicals including opioid antagonist naloxone and naltrexone, aversive agents such as denatonium and capsaicin, black dye and corrosive chemicals such as bleach etc.

A nichrome wire FIG. 6, 25 is connected to the tamper sensors 7. When the tamper sensors are activated by any tampering such as wall perforation or disruption, heating, freezing, liquid or magnetic exposure the tamper sensors 7 activate the nichrome wire 25 which heats up and melts the wax plug 15 causing the medication deactivating chemicals to drain into the medication chamber 4 and deactivate the medication 2

Operation

The loading cap 1 is unlocked for loading by the pharmacist and after the medication chamber 4 is loaded with pills 2 it is locked and programmed and back up batteries replaced, before being dispensed to the patient. At a preprogrammed time when the medication is due, the patient fills up the liquid reservoir 18 with a potable liquid, then enters a password/biometric data into the smartphone 6 which when accepted by the smartphone/ECU 6 activates the stepper motor 11, pushing the dispensing arm 9 out and dropping the pill 2 from the pill slot 10 into the liquid chamber 18 at the bottom, reloading the pill slot 10 with another pill 2 on the return stroke. As shown in drawing FIGS. 4 and 5. The patient drinks the liquid with the dissolved medication pill 2. The next pill 2 can only be dispensed after a preprogrammed period of time has passed. Also for added safety the liquid chamber 18 has to be filled with at least a predetermined minimum quantity of liquid to activate the upper float switch 19 before a medication pill 2 can be dispensed and it has to be emptied and refilled before the next medication pill 2 can be dispensed. A wide angle camera 20 facing the liquid reservoir port 21 is connected to the smartphone/ECU 6 which stores and uploads digital pictures and videos online of the patient drinking the liquid infused with the dissolved medication pill 2 which can be subsequently reviewed using human observers and or image recognition software to deter suctioning and storage of the liquid with dissolved medications 2 for later misuse or abuse. The camera 20 can be activated by information from a light sensor attached to the tip of the port 21.

If any abuse or misuse is detected upon review of uploaded images/video data, the medication dispenser can be remotely locked or the remaining medications in the medication dispenser can be rendered unfit for abuse and misuse by remote activation of the electronically activated chemical deactivation system 12. Similarly if any tampering of the medication dispenser by any meaning including perforation, breakage, heating/burning, cooling/freezing, shock or strong magnetic field or liquid exposure is detected by the tamper sensors 7, the electronically activated chemical deactivation system 12 is activated. The nichrome wire 25 which heats up and melts the wax plug 15 causing the medication deactivating chemicals to drain into the medication chamber 4 and deactivate the medication 2

The medication dispenser is immediately locked up and also starts recording and uploading video via the cellular network to an online data server, immediately when the electronically activated chemical deactivation system 12 is activated. The electronically activated chemical deactivation system 12 has a separate power supply which maintains backup power and stays active even when the ECU/smartphone 6 rechargeable battery is drained. If the back batteries are drained below a predetermined voltage threshold the chemical deactivation system is activated. Passive shock and magnetic sensors FIGS. 7a and 7b and FIGS. 8a and 8b are made of a magnet 41 suspended by a wire spring 42 with a hollow ferrous ring/hemisphere 40. One sensor is aligned vertically and another horizontally. Any shock or strong magnetic exposure causes the magnet to make contact with the ring/hemisphere activating the chemical deactivation system 12. A bimetallic strip is used as a passive temperature sensor to monitor high or low temperatures to prevent tampering attempts at battery inactivation by freezing or heating the medication dispenser Monitoring for penetration/perforation and wall disruption is done using a break wire/trip circuit FIG. 9 incorporated into all the sides, bottom and lid of the medication dispenser. Any breakage of the tripwire circuit 50 would be a sign of tampering and cause activation of the chemical denaturing/deactivation system 12. The sides of the medication dispenser have loops of insulated trip wire, wound under slight tension and closely spaced with only minimal and preferably no space between each loop and is placed inside the outer plastic shell of the device shown in drawing page 9. The wire loops can have slight spacing in between for ease of manufacture and multiple layers are overlapped to eliminate the space in between the loops in order to prevent drilling into the wall of the medication dispenser using a thin drill bit. The slight tension will pull the ends of a broken wire away and trip the circuit. The walls can also be made of a printed circuit board that is printed with wire loop circuits on both sides so that the spacing between the wire loops is overlapped by wire loops on the other side. Additional layering can be used to cover the medication chamber.

The medication dispenser walls and lid can be sealed double walled and pressurized or with partial vacuum similar to a vacuum flask and pressure sensors incorporated in the wall can be used monitor for any sign of change of pressure or loss of vacuum indicating wall disruption and be used to activate the chemical denaturing/deactivation system. Similarly the walls of the medication chamber can also be double walled with partial vacuum or be pressurized and pressure sensors in the inner or outer wall can be used to monitor for any change in pressure to detect tampering. Since the trip wire sensor and pressure sensors involves active monitoring by the ecu/smartphone, it requires constant use of electric power, the system is programmed to drain the rechargeable battery first and when drained then use the replaceable back up battery which can be replaced periodically when medications are refilled. The system is designed to activate the medication deactivation system whenever the backup battery charge falls below a specified threshold such as over longer period of time since last replacement or attempts at freezing or heating the device.

The medication dispenser tamper detection sensors cannot be turned off by the patient but rather only by the pharmacist using a special passcode such as during loading or unloading of medications or by the manufacturer or person approved by the relevant government agency.

PARTS LIST FIG. 3

1 locking cap
2 medication pills
3 spring loaded plungers
4 medication chamber
5 power supply
6 electronic control unit/smartphone
7 tamper sensors and secondary ECU
8 charging port
9 dispensing arm with rack
10 pill slot
11 stepper motor pinion gear
12 medication deactivation system
13 deactivating chemicals
18 liquid reservoir
19 upper and lower float switches
20 wide angle camera
21 port
22 outer wall
24 lock

PARTS LIST FIG. 4 AND FIG. 5

2 medication pills
3 spring loaded plungers
9 dispensing arm with rack
10 pill slot
11 stepper motor pinion gear
18 liquid reservoir
22 outer wall

PARTS LIST FIG. 6

4 medication chamber
7 tamper sensors and secondary ECU
12 medication deactivation system
14 deactivation spring loaded plunger
15 wax plug
25 nichrome wire

PARTS LIST FIGS. 7A AND 7B AND 8A AND 8B 7 tamper sensors and secondary ECU
40 ferrous contacts
41 magnet
42 wire spring

PARTS LIST FIG. 9

7 tamper sensors and secondary ECU
50 break wire/trip wire 10
51 break wire/trip wire circuit perforation sensor The mediation dispenser is reusable and once empty can be brought back to the pharmacy and refilled with medication by the pharmacist and the backup batteries replaced if needed. The medication dispenser is also examined for any signs of tampering or damage before refilling.

The medication dispenser has a watertight locking cap that can be locked and unlocked only by the dispensing pharmacist or authorized person. The locking cap allows access to load and unload the medication dispenser and allows for replacement of the backup battery and for programming the device via access to the communication port via connection such as a usb port. The locking cap is replaced by a different key combination lock every time the medication dispenser is refilled to prevent duplication of keys and unauthorized access and tampering and the ECU records the time and dated every time the locking cap is accessed.

The medication dispenser has equipped with a programmable electronic control unit 6 such as a smartphone such as android or apple phones, mini computers such as a raspberry pi, along with micro controller unit such as USB OTG Ioio board or arduino boards or similar and is equipped with a rechargeable battery and a replaceable backup battery to monitor the tamper sensors 7 and a keypad and or touchscreen to control the device.

Unauthorized access is prevented by using passcode unlocking or use of biometric sensors such as a fingerprint, iris, face ID or other biometric characteristics available to unlock the smartphone.

The medication can be in liquid form and the dispenser equipped with an electronically controlled pump, which when activated allows for a fixed preprogrammed volume of the medication solution to be dispensed at the preprogrammed interval into the liquid reservoir. When the medication is in tablet or powder or capsule form an electronically locked mechanical dispensing arm/knob/lever can be unlocked and pushed/turned by the patient thereby dispensing the medication or an electronically controlled linear actuator or stepper motor is activated which moves the dispensing arm/disc dispensing only one dose of the medicine.

The medication can be specially formulated to be either in liquid form or powder or rapidly dissolving pill and further misuse of the medication can be prevented by addition of gelling and thickening agents to prevent intravenous and intranasal administration of the dispensed medication. Also orally inactive opioid antagonists such as naloxone can be added to the opioid medication to prevent intravenous usage. In order to prevent bitter taste of the medicine the medication can be composed of a rapidly dissolving base with combination of slower dissolving film coated small granules of the medication and food grade fillers.

These denaturing chemicals include one or a combination of multiple chemicals including opiate antagonists such as naloxone and naltrexone, benzodiazepine antagonist such as flumazenil, chemicals that react with and deactivate narcotics and benzodiazepines, aversive agents such as Denatonium and capsaicin, activated charcoal, colored dyes, bleach and various corrosive chemicals, quick setting compounds with glue additives such as plaster of paris, rapid hardening hydraulic cement, drywall mud etc.

The medication chamber of the medication container can be lined on the inside with a heat resistant liner from low thermal conductivity and also be enclosed in a outer vacuum sealed layer and when tampering is detected by activation of any of the tamper sensors the medications inside the medication chamber are deactivated and rendered unfit for misuse and abuse by immediate activation of an electronically triggered exothermic reaction such as mixing of potassium permagnate with glycerin, pyrotechnic, thermite or thermate reaction. The medication dispenser can be equipped with a pressure relief valve to prevent and pressure related explosion.

The medication chamber can also be equipped with a canister made of a brittle material such as glass or acrylic which has an electronically activated pyrotechnic initiator such as an electronic match or gas generator and contains denaturing/deactivating chemicals in liquid form for solid medication and powder or liquid form for liquid medication. Whenever tampering of the medication dispenser is detected the secondary ecu, electronically activates the pyrotechnic initiator with the resulting pressure shattering the canister containing the chemical deactivating agents and mixing them with the medication in the chamber. The cement or plaster of paris will react with the water in the liquid medication and quickly harden, while the activated charcoal will bind to the medication rendering it inactive. Opioid antagonists and other agents added prevent misuse of any active medication that can be extracted for misuse or abuse.

A combination of the above-mentioned chemical and heat based denaturing of the medications can also be employed. The tamper resistant medication dispenser can be programmed to activate the medication deactivating mechanisms at the end of a specified interval when the medical necessity for the prescribed medications is over, such as 2 weeks after surgery when severe pain should have resolved and the remaining unused medications in the medication chamber can be deactivated and rendered unfit for abuse and misuse.

The tamper proof medication dispenser can be equipped with wide angle camera to record pictures and video of the patient taking the medications for further review of medication usage. The camera is activated for a short fixed amount of time when the medication is being sucked from the port via a light sensor located at the tip of the port and will record pictures or video of patient actually ingesting the medications to prevent further misuse by diversion. Motion sensors and float switch information can also be used to activate the camera. The tamper resistant medication dispenser can also incorporate a smart phone ecu with cellular service to record and monitor medication usage by uploading pictures and video to central server where such pictures and video can be reviewed and also to allow for remote reprogramming of the medication dosing interval but only within fixed medically safe predefined parameters (to prevent overdose risk) such as if the patient has significant exacerbation of pain such as after sustaining a fall or injury and higher dosage of medication is needed and is approved by the prescribing physician with the dosing interval being changed remotely. This can also be used to allow for remote activation of the medication deactivation mechanism in the event of misuse or abuse noted upon review of recorded pictures or video from the medication dispenser or change in patient medical condition as determined by the prescribing physician.

The medication dispenser can be equipped with usb port, bluetooth, wifi or cellular connectivity to allow programming of the device. A smartphone with an application to control the medication dispenser can be incorporated within the medication dispenser or be designed to link to the medication dispenser via usb, wifi, bluetooth or similar connectivity acting as the electronic control unit for the device.

Figure 10:
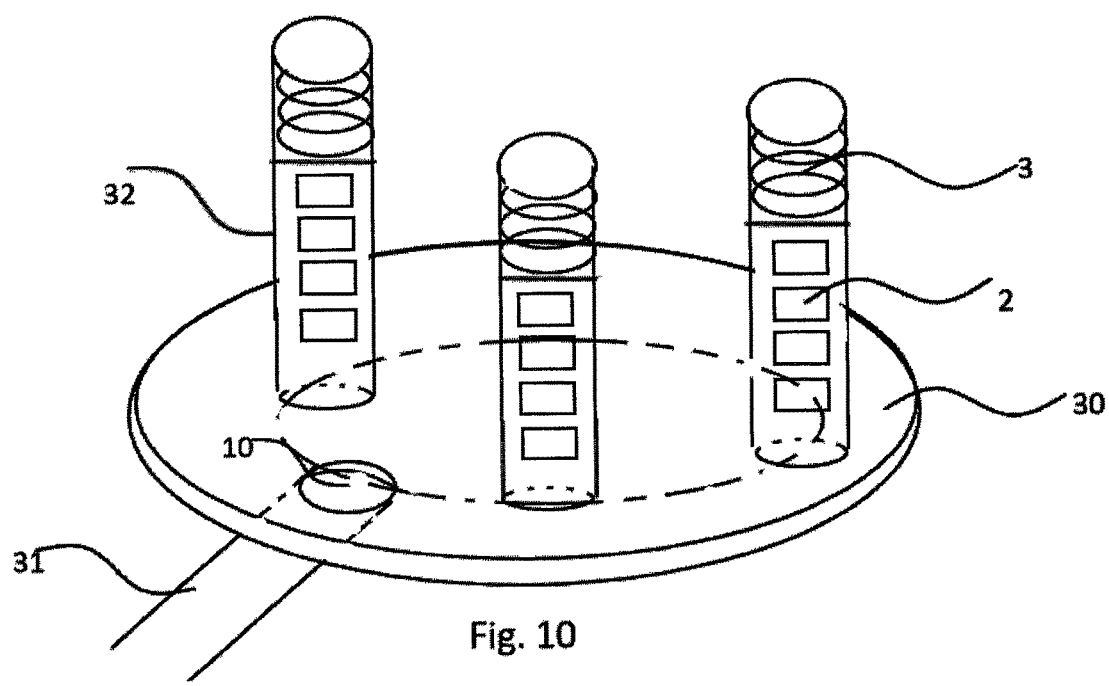

In another embodiment shown in FIG. 10 the pill tubes 32 are arranged in circular fashion placed over a dispensing disc 30 with a pill slot 10 located in the circular path. The rotation of the dispensing disc 30 is controlled by a stepper motor and each rotation of the dispensing disc 30 drops one pill from the pill slot into the chute 31 connected to the liquid reservoir 18. All other features of the embodiment in FIG. 3 are shared with this embodiment.

PARTS LIST FIG. 10

Figure 11:
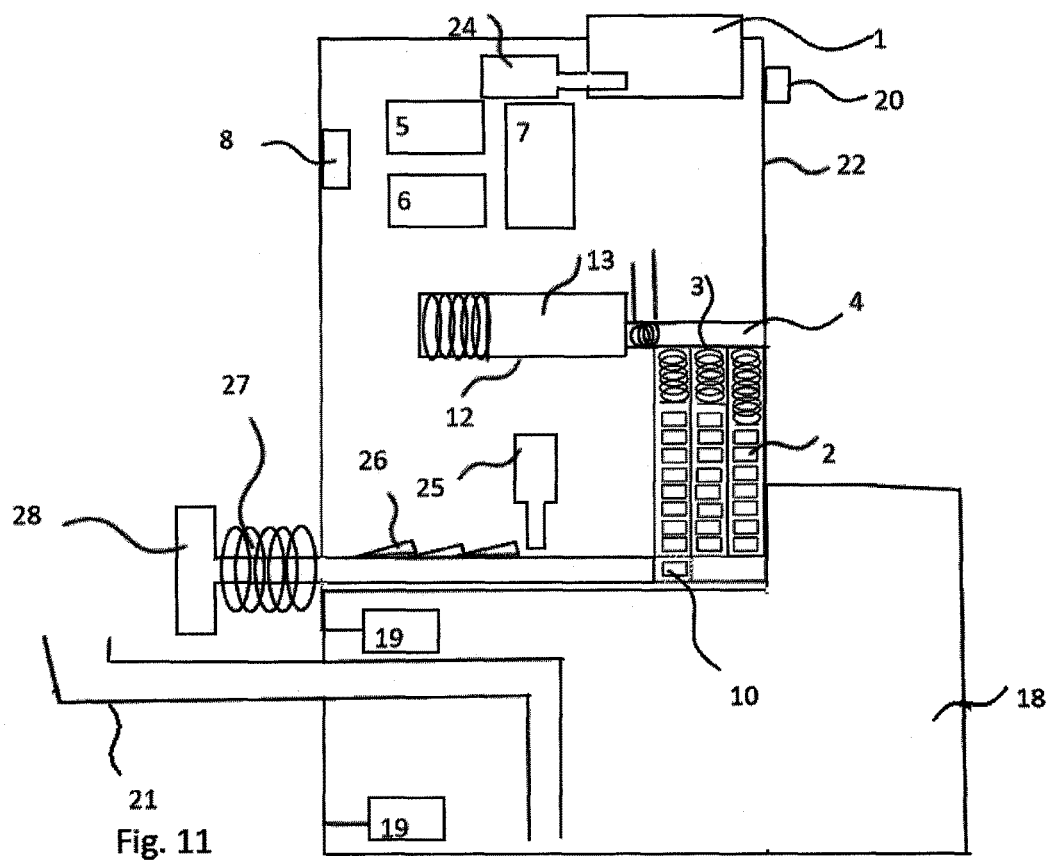

2 medication pills
3 spring loaded plunger
10 pill slot
30 dispensing disc
31 pill chute
32 pill tube In another embodiment as shown in FIG. 11 the medication dispenser has all the features of the embodiment in FIG. 1 however it is also equipped with a smartphone 6, video recording via 20 and tamper sensors 7 and electronically activated chemical deactivation system 12.

PARTS LIST FIG. 11

1 locking cap
2 medication pills
3 spring loaded plungers
4 medication chamber
5 power supply
6 smart phone electronic control unit
7 tamper sensors and secondary ECU
8 charging port
10 pill slot
12 medication deactivation system
13 deactivating chemicals
18 liquid reservoir
19 upper and lower float switches
20 wide angle camera
21 port
22 outer wall
24 lock
25 electronic lock
26 ratchet teeth
27 push button dispensing arm return spring
28 push button dispensing arm In another embodiment The medication chamber 4 is filled with medication in liquid form instead of pills and an electronically activated pump 70 controlled by the smartphone 6 acting as the primary electronic control unit is used to dispense a preprogrammed volume of medication into the liquid reservoir 18. All other features as described in the embodiment as shown in FIG. 3 are included except for the pill holding and dispensing mechanism.

Figure 13:
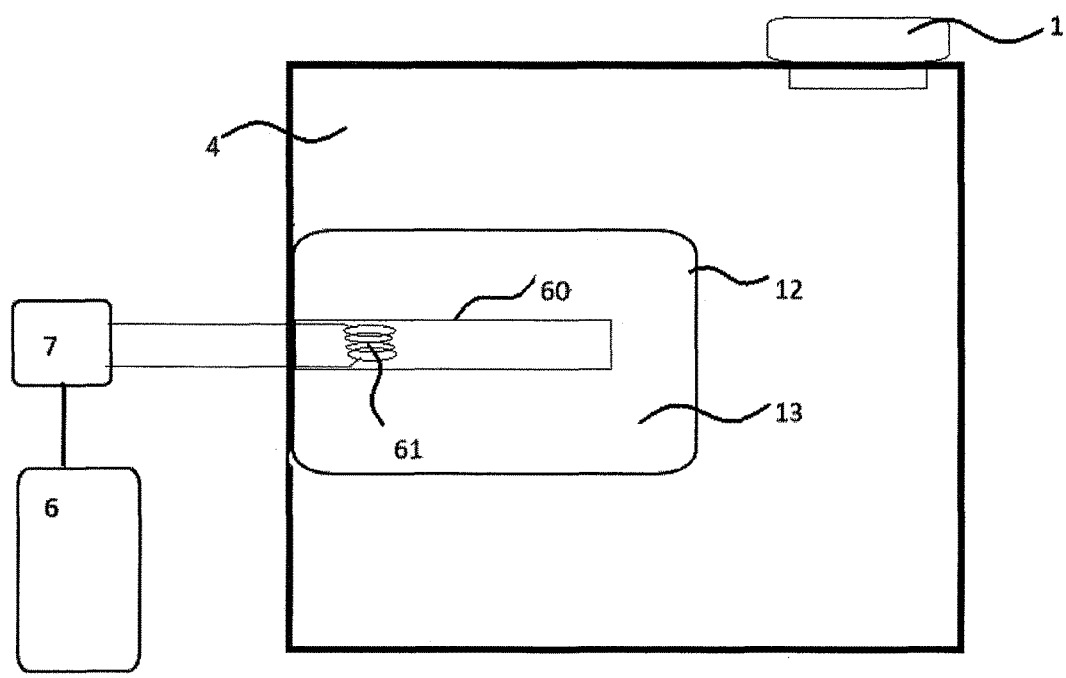

In another embodiment as shown in FIG. 12 and FIG. 13

The medication chamber 4 is filled with medication in liquid form instead of pills and an electronically activated pump 70 controlled by the smartphone 6 acting as the primary electronic control unit is used to dispense a preprogrammed volume of medication into the liquid reservoir 18.

The watertight locking cap 1 is unlocked by the pharmacist to replace backup battery and to refill liquid medication in the medication chamber 4. Within the medication chamber 2 is the electronically activated chemical deactivation system 12 which in this embodiment is a waterproof canister containing medication deactivating chemicals made of a brittle material such as glass or acrylic which has a sealed electronically activated gas generator surrounded by denaturing/deactivating chemicals 13 containing cement, plaster of paris and activated charcoal, naloxone and other chemicals such as coffee grounds, kitty litter, limestone etc as described above as mentioned above in powder form. Whenever tampering of the medication dispenser is detected the ecu/smartphone 6 electronically activates the gas generator with the resulting pressure shattering the canister containing the chemical deactivating agents 13 and mixing them with the liquid medication in the medication chamber 4. The cement and plaster of paris will react with the water in the liquid medication and quickly harden, while the activated charcoal will bind to the medication rendering it inactive. Opioid antagonists and other caustic agents added prevent misuse of any active medication that can be extracted for misuse or abuse. All other features as described in embodiment in FIG. 3 are included except for the pill holding and dispensing mechanism and different design and function of the electronically activated medication deactivation system.

PARTS LIST FOR FIG. 12

1 locking cap
4 medication chamber
5 power supply
6 electronic control unit/smartphone
7 tamper sensors and secondary ECU
12 medication deactivation system containing deactivating chemical
18 liquid reservoir
19 upper and lower float switches
20 wide angle camera
21 port
22 outer wall
60 electronically activated pyrotechnic initiator/gas generator
70 electronic pump

PARTS LIST FOR FIG. 13

Figure 14:
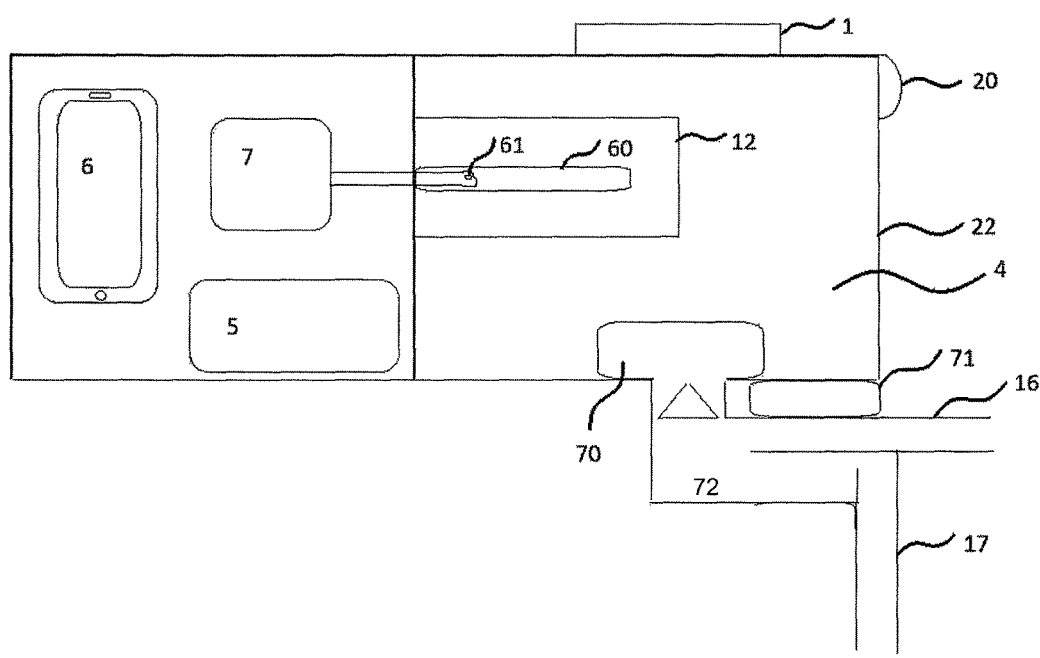

1 locking cap
4 medication chamber
6 electronic control unit/smartphone
7 tamper sensors and secondary ECU
12 medication deactivation system containing deactivating chemical
60 electronically activated pyrotechnic initiator/gas generator
61 bridgewire In another embodiment as shown in FIG. 14

The medication dispenser has all the features of the embodiment in FIG. 12 except the liquid reservoir 18, port 21 and float switches 19. Instead the medication dispenser is equipped with an inlet port 17 and outlet port 16 and flowmeter 71 and a dispensing reservoir 72.

Medication is in liquid form preferably thick liquid or gel form Operation When the medication is due and the patient presses the dispense button on the medication dispenser app in the smartphone 6 after biometric verification to access the smartphone 6. A predetermined dose of liquid medication in the medication chamber 4 is dispensed by the electronic pump 70 activated by the smartphone 6 into the dispensing chamber 72. The patient places the inlet port 17 which is shaped like a drinking straw into a cup of liquid and places the outlet port 16 in his mouth and sucks which draws liquid from the cup via the inlet port 17 and through the dispensing reservoir 72 where the liquid mixes with the medication and the patient swallows the medication infused liquid. The medication is preferably a thick liquid/gel and requires a large volume of liquid to pass through the dispensing reservoir in order to fully dissolve. A flowmeter 71 measures the amount of liquid passing through the dispensing reservoir 72 and the patient is instructed to at least drink a minimum volume of liquid. The next dose is dispensed only when a minimum volume of liquid has passed through the dispensing reservoir 72 as determined by flowmeter 71. The camera 20 can be triggered by the flowmeter 71 sensing flow through the dispensing reservoir 72.

PARTS LIST FIG. 14

1 locking cap
4 medication chamber
5 power supply
6 electronic control unit/smartphone
7 tamper sensors and secondary ECU
12 medication deactivation system containing deactivating chemical
16 outlet port
17 inlet port
20 wide angle camera
22 outer wall
60 electronically activated pyrotechnic initiator/gas generator
61 bridgewire
70 electronic pump
71 flowmeter
72 dispensing reservoir In another embodiment rapid dissolving medication pills can be dispensed into the dispensing reservoir 72 instead of liquid medication in the above embodiment and all the features of embodiments in FIGS. 1, 2, 3 and 11 are used except the liquid reservoir 18, port 21 and float switches 19. Instead the medication dispenser is equipped with an inlet port 17 and outlet port 16 and flowmeter 71 and a dispensing reservoir 72.

I claim:

1. A secure medicine dispenser, comprising:
   a sealed or lockable medicine chamber having an opening for dispensing a medicine;
   a fluid reservoir;
   a dispensing mechanism coupled to the opening for receiving the medicine and for dispensing the medicine into the fluid reservoir;
   a sensor for detecting the level of fluid in the fluid reservoir and outputting a signal when a predetermined fluid level is detected; and
   an electronic control unit to receive a medicine dispense signal and the signal from the sensor wherein the electronic control unit only causes the dispensing mechanism to dispense the medicine into the fluid reservoir when the medicine dispense signal and the sensor signal is received.

2. The secure medicine dispenser in claim 1, wherein the sensor is a float sensor.

3. The secure medicine dispenser I claim 1, further comprising a video recorder to record the consumption of the dispensed medication.

4. The sure medicine dispenser in claim 3, wherein the video recorder is a smart phone and wherein the smart phone is used to control operations of the medicine dispenser.

5. The secure medicine dispenser in claim 1, further comprising a tamper sensor to detect an intrusion into the medicine chamber.

6. The secure medicine dispenser in claim 5, wherein the tamper sensor is an electrical trip wire.

7. The secure medicine dispenser in claim 6, further comprising a thermal or chemical system to render the medicine unfit for misuse in response to the tamper sensor detecting an event.

8. The secure medicine dispenser in claim 1, further comprising a timer wherein the medicine dispense signal is output at a predetermined time based on the timer.

* * * * *